US00PP23956P3

(12) United States Plant Patent
Larse

(10) Patent No.: US PP23,956 P3
(45) Date of Patent: Oct. 8, 2013

(54) STRAWBERRY PLANT NAMED 'CUPCAKE'

(50) Latin Name: *Fragaria×ananassa*
Varietal Denomination: CUPCAKE

(75) Inventor: John Larse, Aptos, CA (US)

(73) Assignee: Sweet Darling Sales, Inc., Aptos, CA (US)

( * ) Notice: Subject to any disclaimer, the term of this patent is extended or adjusted under 35 U.S.C. 154(b) by 0 days.

(21) Appl. No.: 13/373,705

(22) Filed: Nov. 28, 2011

(65) Prior Publication Data

US 2013/0139286 P1 May 30, 2013

(51) Int. Cl.
*A01H 5/00* (2006.01)

(52) U.S. Cl.
USPC ..... Plt./209

(58) Field of Classification Search
USPC ..... Plt./209
See application file for complete search history.

*Primary Examiner* — Annette Para
(74) *Attorney, Agent, or Firm* — Cooley LLP

(57) ABSTRACT

The present invention provides a new and distinct strawberry variety designated as 'Cupcake' (a.k.a., '107615').

7 Drawing Sheets

Latin name of genus and species: *Fragaria×ananassa.*
Varietal denomination: 'CUPCAKE'.

BACKGROUND OF THE INVENTION

The present invention relates to a new and distinct early day-neutral strawberry variety designated as 'CUPCAKE' (a.k.a. '107615'). This new variety is the result of a controlled-cross between a female parent cultivar designated '102213' and a male parent cultivar designated '1581' (both unpatented, proprietary cultivars) made by the inventor and first fruited in Watsonville, Calif. growing fields.

Following selection and during testing, the plant was originally designated '107615' and subsequently named 'CUPCAKE'. The new variety of 'CUPCAKE' was asexually reproduced via runners (stolons) by the inventor at Watsonville, Calif. Asexual propagules from the original source have been tested in the Watsonville growing fields and to a limited extent, growing fields in low and high elevation. The properties of this variety were found to be transmissible by such asexual reproduction. The cultivar is stable and reproduces true to type in successive generations of asexual reproduction.

SUMMARY OF THE INVENTION

This invention relates to a new and distinctive early producing day-neutral type cultivar designated as 'CUPCAKE'. It is primarily adapted to the climate and growing conditions of the central coast of California. This region provides the necessary temperatures required for it to produce a strong vigorous plant and to remain in fruit production from April through October. The nearby Pacific Ocean provides the needed humidity and moderate day temperatures and evening chilling to maintain fruit quality for the production months.

The following traits in combination distinguish strawberry variety 'CUPCAKE' from the known strawberry varieties. Plants for the botanical measurements in the present application were grown as annuals. In the following description, color references are made to The Royal Horticultural Society Colour Chart, 1995 Edition, except where general terms of ordinary dictionary significance are used.

The following are the most outstanding and distinguishing characteristics of this new variety when grown under normal conditions in Watsonville, Calif.

Large fruit.
Bruising resistant, and
Weather resistant.

The produced fruit is attractive and of excellent quality. Produced fruit is pink red to light-red at maturity, medium to large in size, firm to very firm, conical to cylindrical in shape with a smooth surface lacking creases. Seeds are slightly sunken below the surface.

'CUPCAKE' is primarily adapted to the growing conditions of the central coast of California, characterized by foliage small to medium in size and light to medium green in color. Production generally begins in April and produces continually into October with 40% to 50% of its production in the months of August through September.

When 'CUPCAKE' is compared to the proprietary female parent '102213', 'CUPCAKE' forms a taller and more vigorous plant with larger fruit.

When 'CUPCAKE' is compared to the proprietary male parent '1581', 'CUPCAKE' is more resistant to bruising and, therefore, also more rain resistant.

When 'CUPCAKE' is compared to 'Albion' (U.S. Plant Pat. No. 16,228), the commercially distinguishing features are significantly bigger fruit, higher resistance to bruising, and higher resistance to weather variations. Additionally, 'CUPCAKE' has a later harvest interval than 'Albion' and features slightly smaller leaves with higher concavity.

DESCRIPTION OF THE DRAWINGS

The accompanying color photographs depict various characteristics of the 'CUPCAKE' cultivar at various stages of development as nearly true as possible to make color reproductions.

DETAILED BOTANICAL DESCRIPTION

Figure 1:
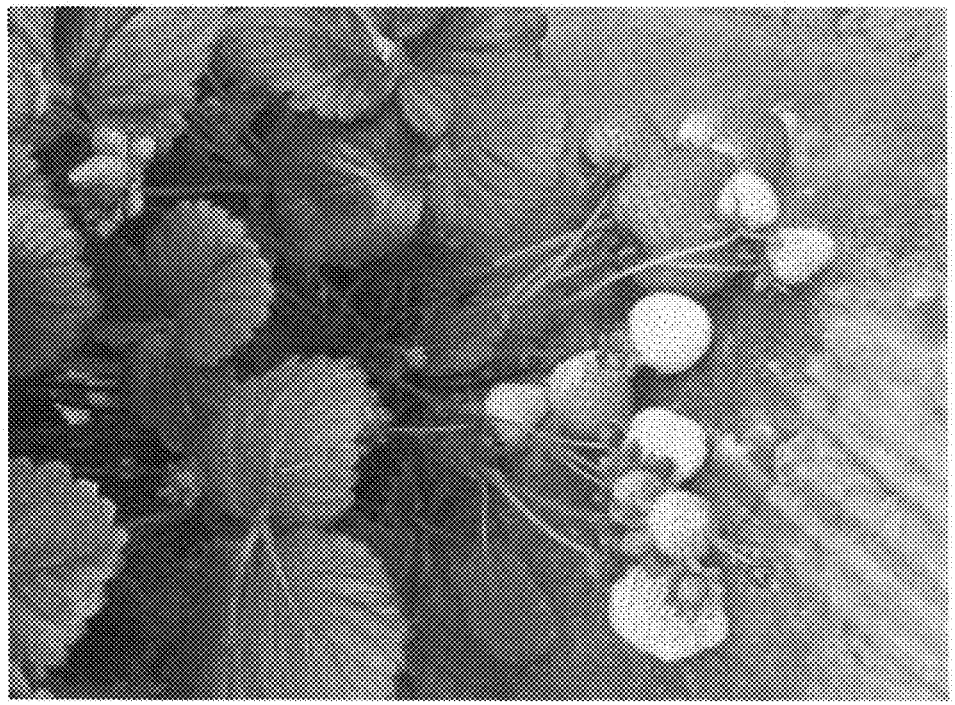
FIG. 1 shows the plant in its production stage bearing fruit.
Figure 2:
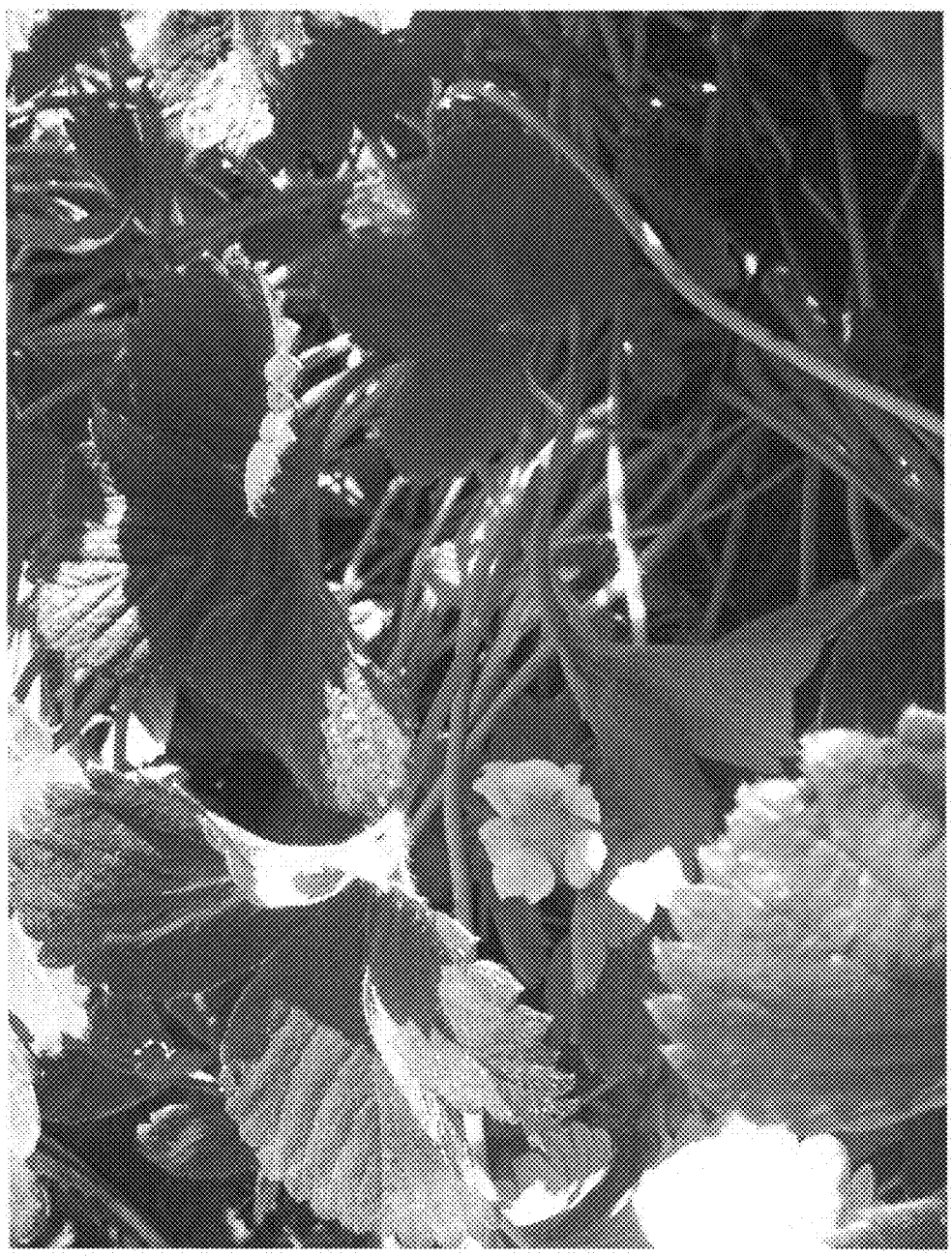
FIG. 2 shows the plant with flower and runners.
Figure 3:
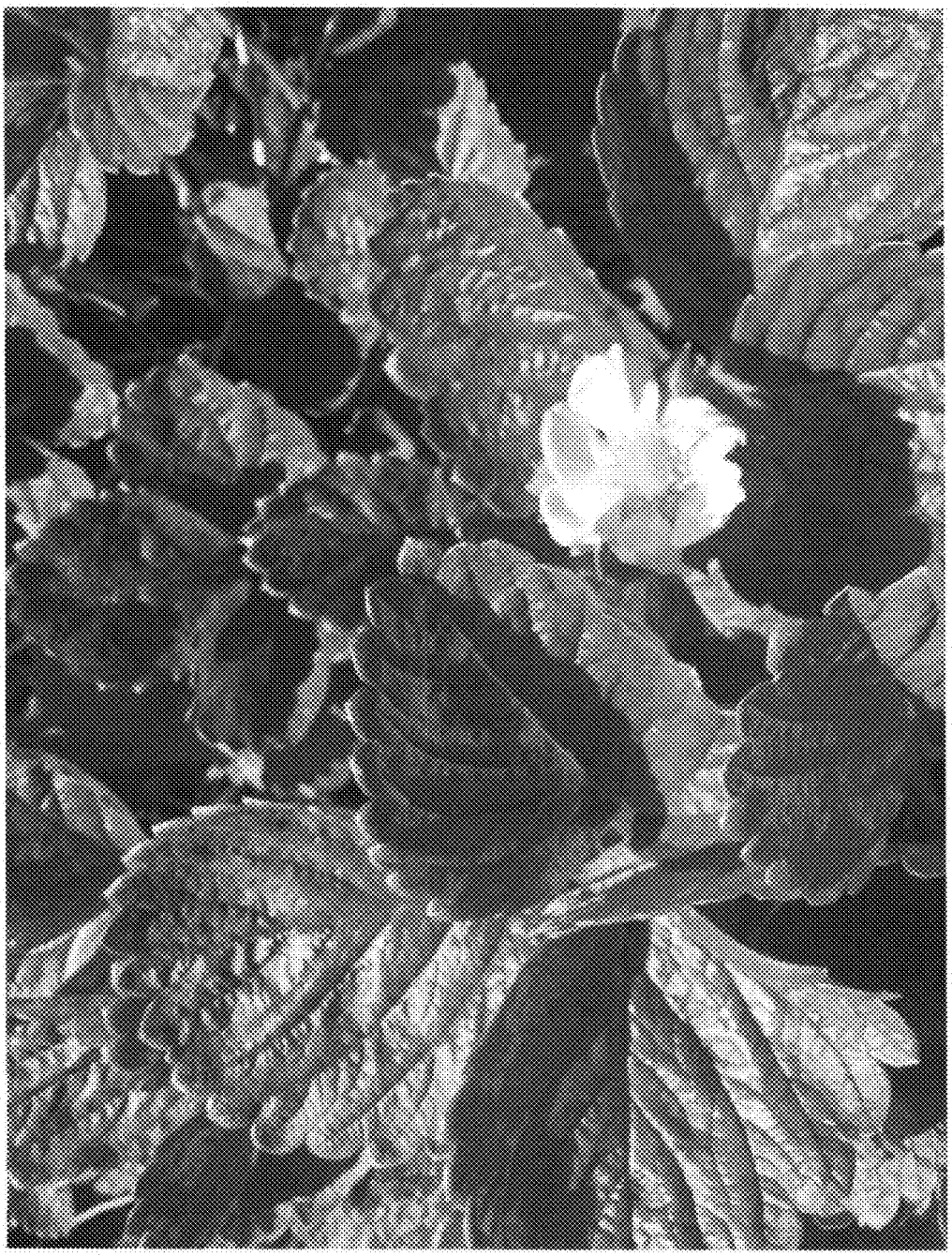
FIG. 3 shows typical leaves in the production cycle.
Figure 4:
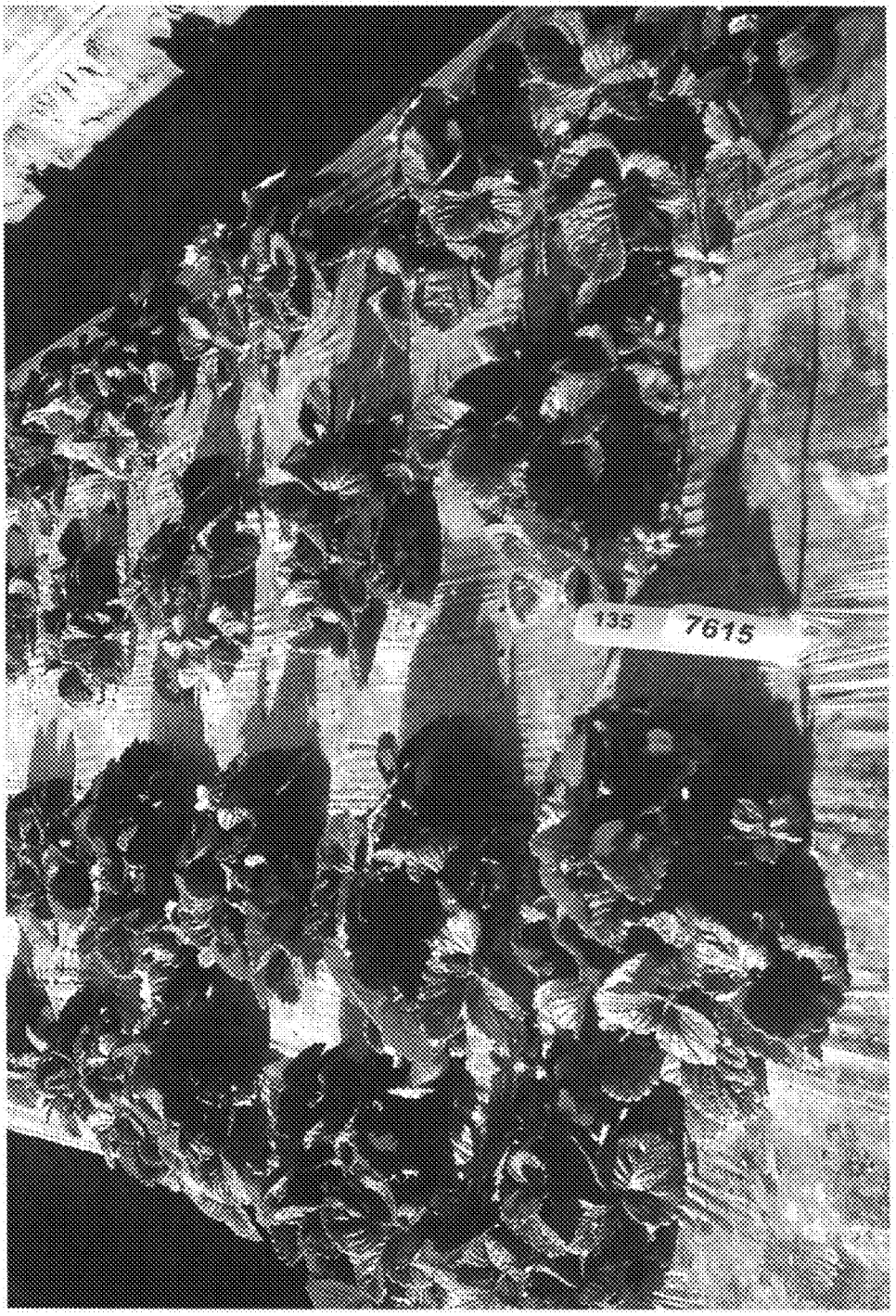
FIG. 4 shows 'CUPCAKE' plants in the field.
Figure 5:
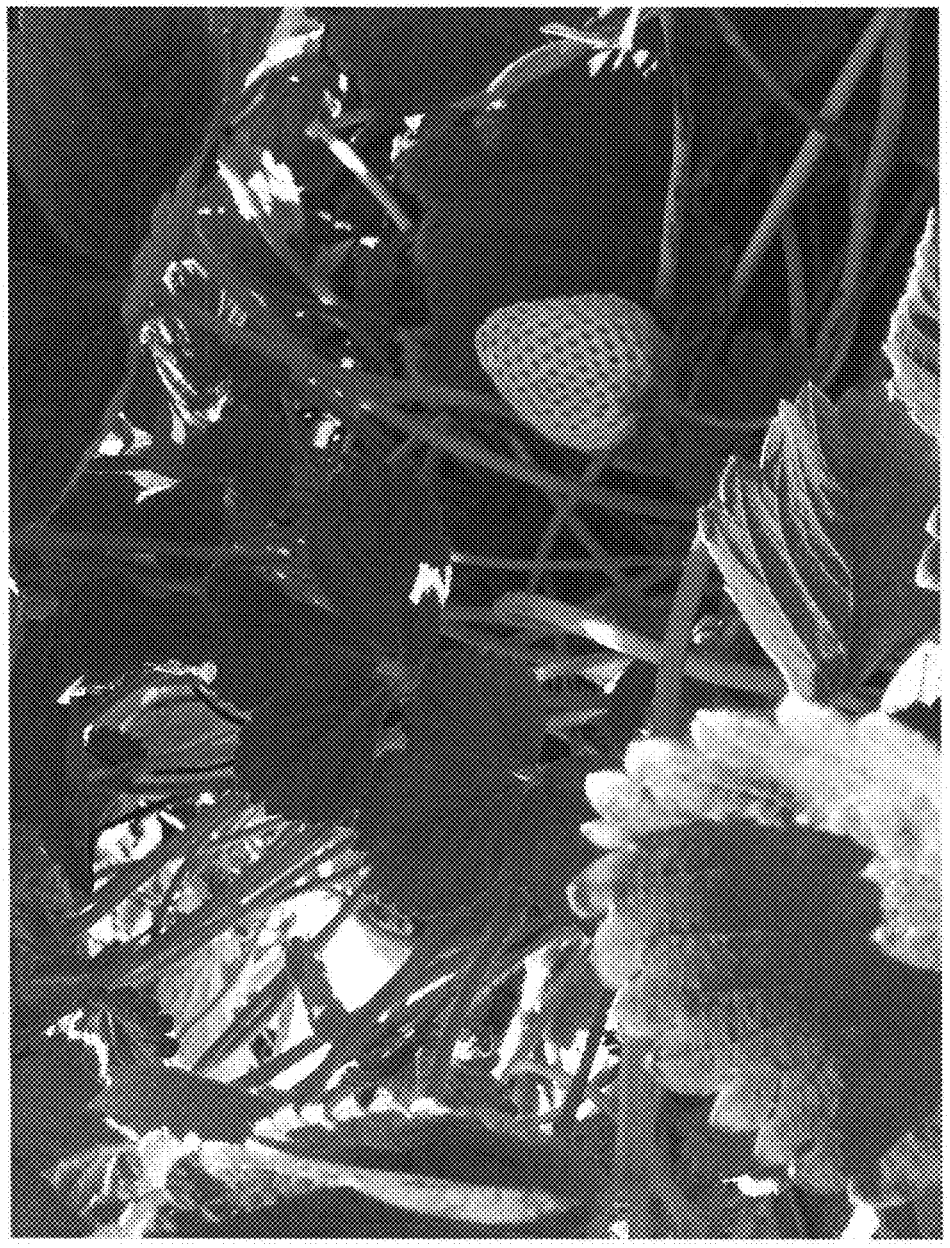
FIG. 5 shows the plant with unripe fruit and runners.
Figure 6:
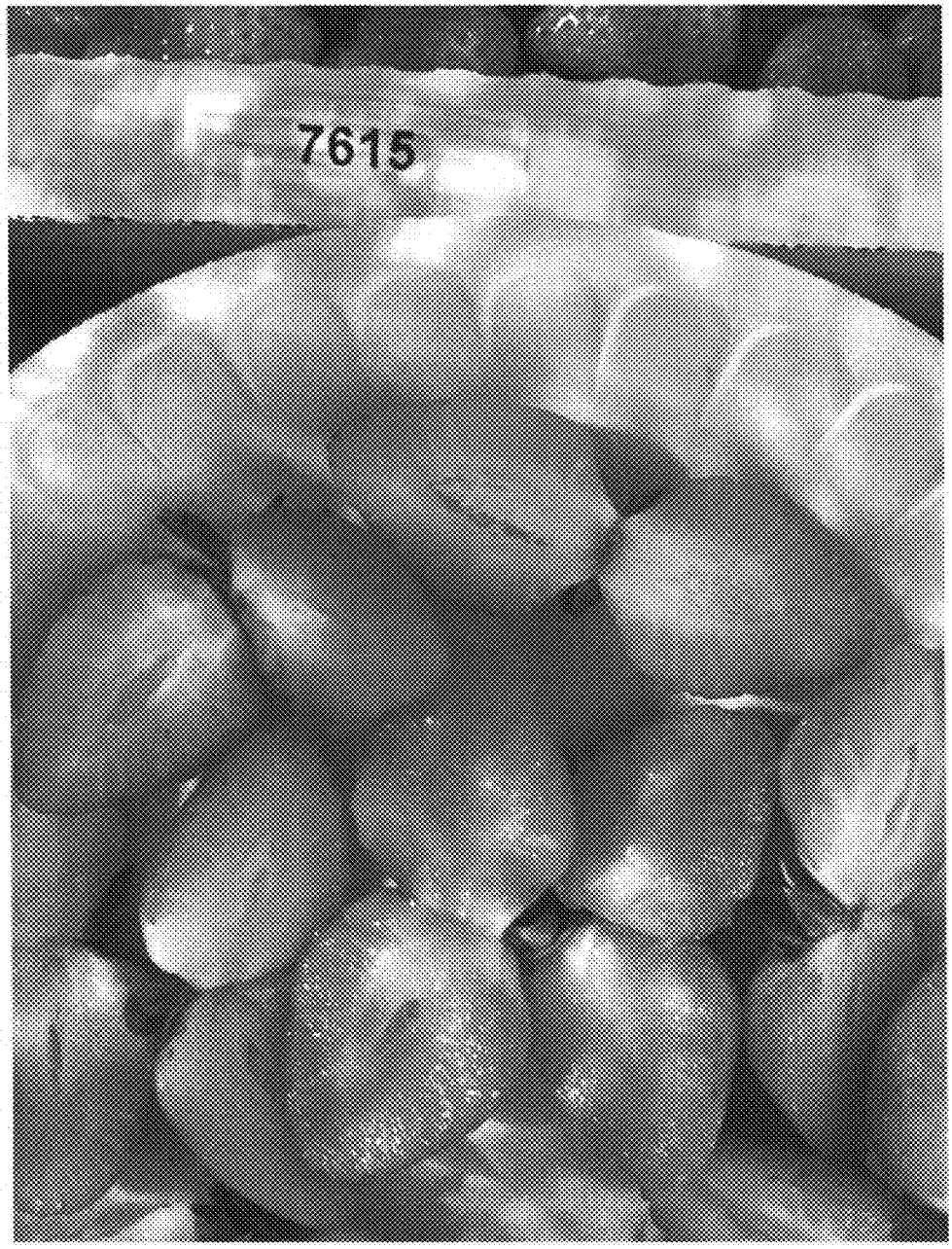
FIG. 6 shows sliced 'CUPCAKE' fruit.
Figure 7:
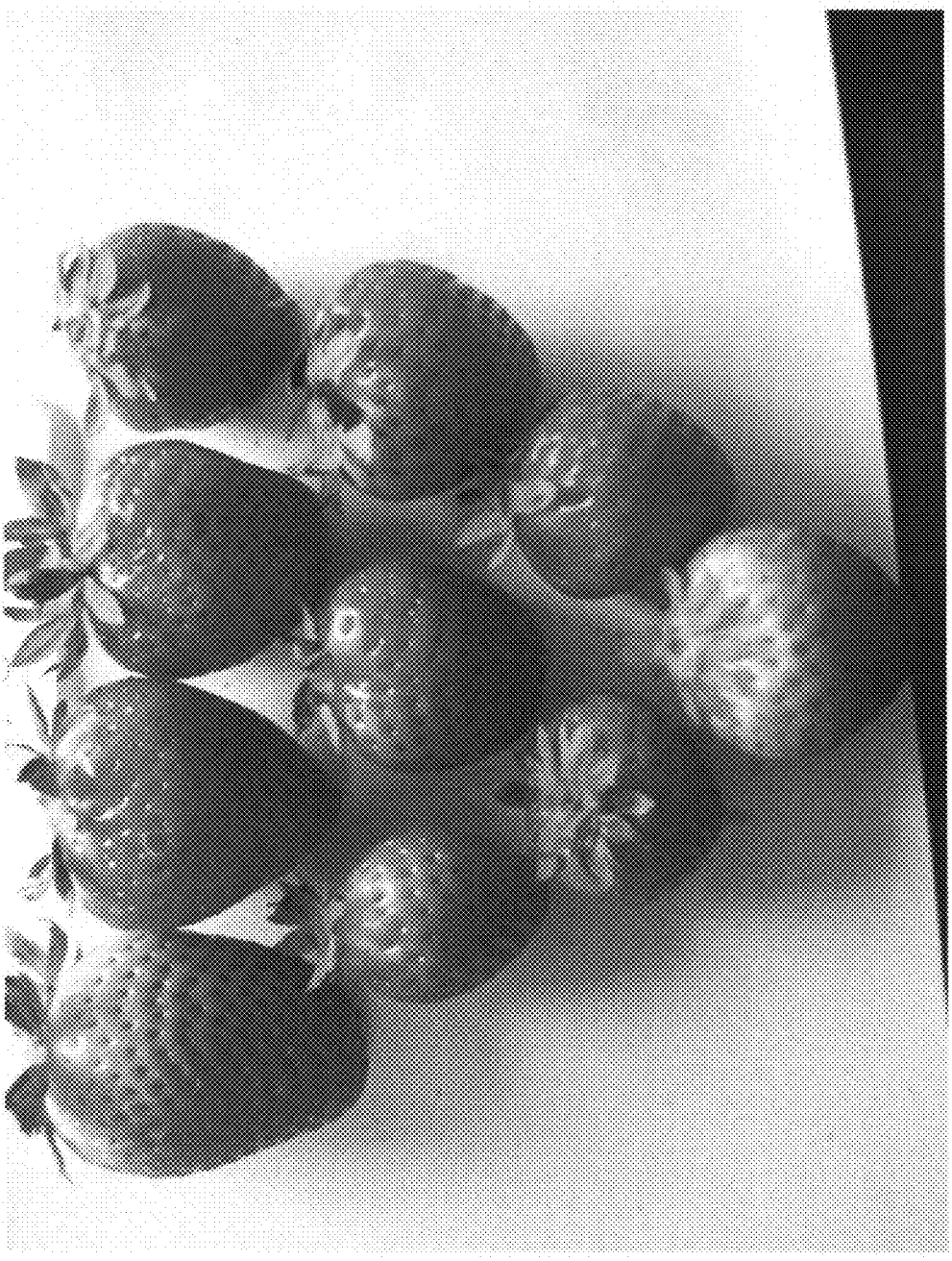
FIG. 7 shows ripe and near-ripe 'CUPCAKE' fruits.

This invention relates to a new and distinctive day-neutral (ever-bearing) type cultivar designated as 'CUPCAKE', but may be considered a weak day-neutral in that it is somewhat similar to a short day. When grown in moderate, coastal climates 'CUPCAKE' loads up with larger fruit in the year before the summer solstice, but with an extended harvest period of fairly heavy volume into autumn season. 'CUPCAKE''s fruit is medium to large in size, that is relatively firm to very firm, mostly conical to cylindrical shape and some wedge shape with seeds slightly sunken below the surface.

Among the characteristics that distinguish the new variety from the other closely related varieties are the timing of fruiting, plant vigor, position of the inflorescences, leaf morphology, leaf size, leaf density, leaf color, and disease and pest resistance.

'CUPCAKE' has not been observed under all possible environmental conditions, and the phenotype may vary significantly with variations in environment. The following observations, measurements, and comparisons describe this plant as grown at California, when grown in the field, unless otherwise noted. As stated above, the color determination is in accordance with The Royal Horticultural Society Colour Chart, 1995 Edition, except where general color terms of ordinary dictionary significance are used. Plants for the botanical measurements in the present application are annual plants.

Botanical classification: 'CUPCAKE' is a fertile hybrid derived from a cross.

Common name: Garden strawberry.

General description:

*Plant habit.*—Moderate, coastal climates.

The following description is applied to our plants that are 5 months old as of the time of the measurements.

Classification:

*Species.*—*Fragaria×ananassa.*

*Common name.*—Garden Strawberry.

*Denomination.*—'CUPCAKE'.

Parentage:

*Female parent.*—'102213'.

*Male parent.*—'1581'.

Plant:

*Height.*—12.7 cm.

*Diameter.*—13.1 cm.

*Habit.*—Globose, upright.

*Density.*—Medium.

*Vigor.*—Strong.

Terminal leaflet:

*Length.*—8.4 cm.

*Width.*—8.3 cm.

*Length/width ratio.*—Approximately One.

*Shape in cross-section.*—Concave.

*Blistering.*—Low.

*Glossiness.*—Medium.

*Average number of leaflets.*—Exactly 3.

*Color above.*—Dark Green (RHS 137A).

*Color below.*—Green (RHS 139C).

*Shape.*—Orbicular.

*Margin.*—Crenate to Serrate.

*Venation pattern.*—Reticulate. The shape of the base is obtuse and light to medium in density. No bract leaves were observed in samples. The leaves are moderately to highly glossy.

Petiole:

*Length.*—9.4 cm.

*Width.*—4.1 cm.

*Color.*—Yellow Green (RHS 145A).

Petiolule:

*Length.*—4.3 mm.

*Width.*—2.6 mm.

*Color.*—Yellow Green (RHS 145A).

Stolon:

*Average daughters/plant.*—About one.

*Diameter.*—4.1 mm.

*Color.*—Dark Purple Red (RHS 53A).

Inflorescence:

*Position relative to foliage.*—At same level.

*Average petals/flower.*—6.5.

*Petal length.*—15.7 mm.

*Petal width.*—15.8 mm.

*Petal length/width ratio.*—About one.

*Petal shape/base.*—Orbicular.

*Petal apex.*—Round.

*Petal margin.*—Entire.

*Petal spacing.*—Slightly overlapping.

*Petal color.*—White (RHS 157B).

*Corolla.*—38.7 mm.

*Sepal length.*—23.3 mm.

*Sepal width.*—13.1 mm.

*Sepal length/width ratio.*—1.8.

*Sepal color.*—Dark Green (RHS 137A).

*Calyx.*—48.3 mm (Diameter relative to corolla: Larger).

*Peduncle.*—13.4 cm.

*Stipule frequency.*—Low. The positioning of the inflorescence is even with or slightly below foliage.

Fruit:

*Fruit truss attitude.*—Prostrate.

*Average fruit/truss.*—About one.

*Relative size.*—Large.

*Fruit length.*—42.3 mm.

*Fruit width.*—42.1 mm.

*Fruit length/width ratio.*—1.01.

*Surface color.*—Red (RHS 45A).

*Flesh color.*—Orange Red (RHS 41B).

*Core color.*—White (RHS 155C).

*Shape.*—Predominately conical.

*Average weight/fruit.*—31.5 g.

*Average weight/plant.*—105.1 g.

*Hollow core length.*—31.7 mm.

*Hollow core width.*—9.7 mm.

*Hollow core length/width ratio.*—3.3.

*Insertion of achenes.*—Slightly indented.

*Average achenes/fruit.*—247.

*Firmness of flesh.*—Firm.

*Glossiness.*—Strong.

*Sweetness.*—Medium. The fruit's flavor is consistently good or better than good throughout the season.

Variety identification testing for 'CUPCAKE': No matches to existing cultivars were found using SSR marker testing in a commercial database search.

The invention claimed is:

1. A new and distinct cultivar of strawberry plant named 'Cupcake' substantially as shown and described herein.

* * * * *